United States Patent [19]
Williams et al.

[11] Patent Number: 5,817,911
[45] Date of Patent: Oct. 6, 1998

[54] TRANSGENIC MICE EXPRESSING ALVEOLAR MCP-1

[75] Inventors: Lewis T. Williams, Tiburon; Michael Dee Gunn, San Francisco, both of Calif.

[73] Assignee: Regents of the University of California, Alameda, Calif.

[21] Appl. No.: 420,001

[22] Filed: Apr. 7, 1995

[51] Int. Cl.[6] ............................ C12N 15/63; C12N 15/00; A61K 48/00

[52] U.S. Cl. .......................... 800/2; 435/172.3; 435/69.1; 424/9.1

[58] Field of Search ............................... 800/2; 435/320.1, 435/172.3, 240.2, 69.1; 935/62, 56, 53, 70; 424/9.1

[56] References Cited

U.S. PATENT DOCUMENTS

| | | | |
|---|---|---|---|
| 4,399,216 | 8/1983 | Axel et al. | 435/6 |
| 4,873,191 | 10/1989 | Wagner et al. | 435/172.3 |
| 5,241,049 | 8/1993 | Goodman et al. | 530/350 |
| 5,387,742 | 2/1995 | Cordell | 800/2 |
| 5,470,560 | 11/1995 | Martin, Jr. | 424/9.2 |

OTHER PUBLICATIONS

Hill et al., "Defect in neutrophil granulocyte chemotaxis in job's syndrome of recurrent 'cold' staphylococcal abscesses," *Lancet* 2:617–619 (1974).
Chang et al., "Tumour–specific transplantation antigen from SV40 transformed cells binds to DNA," *Nature* 269:438–440 (1977).
Fiers et al., "Complete nucleotide sequence of SV 40 DNA," *Nature* 273:113–120 (1978).
Holland, "Isolation and identification of yeast messenger ribonucleic acids coding for enolase, glyceraldehyde–3–phosphate dehydrogenase, and phosphoglycerate kinase," *Biochemistry* 17(23):4900–4907 (1978).
Stinchcomb et al., "Isolation and characterisation of a yeast chromosomal replicator," *Nature* 282:39–43 (1979).
Beck, "Nucleotide sequence of the gene ompA coding the outer membrane protein II* of *Escherichia coli* K–12," *Nucleic Acids Research* 8:3011–3027 (1980).
Goeddel et al., "Synthesis of human fibroblast interferon by *E. coli*," *Nucleic Acids Research* 8:4057–4074 (1980).
Hitzeman, "Isolation and characterization of the yeast 3–phosphoglycerokinase gene (PGK) by an immunological screening technique," *J. Biol. Chem.* 255(24):12073–12080 (1980).
Hunninghake et al., "Human alveolar macrophage–derived chemotactic factor for neutrophils," *J. Clin. Invest.* 66:473–483 (1980).
Merrill et al., "Alveolar macrophage–derived chemotactic factor, Kinetics of in vitro production and partial characterization," *J. Clin. Invest.* 65:268–276 (1980).
Tschumper et al., "Sequence of a yeast DNA fragment containing a chromosomal replicator and the TRP1 gene," *Gene* 10:157–166 (1980).
Hunninghake et al., "Mechanisms of neutrophil accumulation in the lungs of patients with idiopathic pulmonary fibrosis" *J. Clin. Invest.* 68:259–269 (1981).
Kikuchi et al., "The nucleotide sequence of the promoter and the amino–terminal region of alkaline phosphatase structural gene (phoA) of *Escherichia coli*," *Nucleic Acids Research* 9(21)5671–5678 (1981).
O'Hare et al., "Transformation of mouse fibroblasts to methotrexate resistance by a recombinant plasmid expressing a prokaryotic dihydrofolate reductase," *Proc. Natl. Acad. Sci. USA* 78(3):1527–1531 (1981).
Shimatake et al., "Purified λ regulatory protein c II positively activates promoters for lysogenic development," *Nature* 292:128–132 (1981).
Seeburg, Peter H., "The human growth hormone gene family: nucleotide sequences show recent divergence and predict a new polypeptide hormone" *DNA* 1:239–249 (1982).
Karin et al., "Human metallothionein genes—primary structure of the metallothionein–II gene and a related processed gene," *Nature* 299:797–803 (1982).
Bitterman et al., "Mechanisms of pulmonary fibrosis" *J. Clin. Invest.* 72:1801–1813 (1983).
Broach, "Construction of high copy yeast vectors using 2–$\mu$m circle sequences," *Meth. Enz.* 101:307–324 (1983).
Clarke, "Selection procedure for isolation of centromere DNAs from *saccharomyces cerevisiae*," *Meth. Enz.* 101:300–307 (1983).
Martin et al., "Leukotriene $B_4$ production by the human alveolar macrophage: A potential mechanism for amplifying imflammation in the lung[1-3]" *Am. Rev. Resp. Dis.* 129:106–111 (1984).
Hammer et al., "Production of transgenic rabbits, sheep and pigs by microinjection," *Nature* 315:680–683 (1985).

(List continued on next page.)

Primary Examiner—Jasemine C. Chambers
Assistant Examiner—Karen M. Hauda
Attorney, Agent, or Firm—Pamela J. Sherwood; Bozicevic & Reed LLP

[57] ABSTRACT

A transgenic, non-human animal is provided which overexpresses a gene responsible for the accumulation of monocytes and leukocytes. The animal is preferably a mammal and more preferably a mouse, rat or guinea pig. The transgenic animal is created by artificially inserting a transgene into a fertilized egg of the animal which egg is then inserted within a pseudo pregnant female where it is allowed to grow. The transgene preferably expresses human Monocyte Chemoattractant Protein-1 (MCP-1) and more preferably overexpresses MCP-1 in type II pulmonary epithelial cells. The invention includes DNA constructs and vectors containing the constructs with a particularly preferred vector being SPC-MCP-1. The plasmid SPC-MCP-1 includes a promoter operatively linked to a human MCP-1 coding sequence. The transgenic animal provides a useful animal model for testing drugs for their efficacy with respect to the treatment of diseases and conditions which result in an acceptable high accumulation of monocytes and/or lymphocytes.

6 Claims, 1 Drawing Sheet

OTHER PUBLICATIONS

Bucchini et al., "Pancreatic expression of human insulin gene in transgenic mice" *Proc. Natl. Acad Sci. USA* 83:2511–2515 (1986).

Hess, "Cooperation of a glycolytic enzymes," *Adv. Enzyme Reg.* 7:149–167 (1986).

Martin et al., "Relative contribution of leukotriene $B_4$ to the neutrophil chemotactic activity produced by the resident human alveolar macrophage," *J. Clin. Invest.* 80:1114–1124 (1987).

Maunder et al., "Procoagulant activity in bronchoalveolar lavage in the adult respiratory distress syndrome: contribution of tissue factor associated with factor VII," *Am. Rev. Respir. Dis.* 135:A260 (1987).

Pinkert et al., "An albumin enhancer located 10 kb upstream functions along with its promoter to direct efficient, liver--specific expression in transgenic mice," *Genes & Dev.* 1:268–276 (1987).

Pollok et al., "Molecular basis of the cell–surface expression of immunoglobulin in $\mu$ chain without light chain in human B lumphocytes," *Proc. Natl. Acad. Sci. USA* 84:9199–9203 (1987).

Schroder et al., "Purification and partial biochemical characterization of a human monocyte–derived, neutrophil–activating peptide that lacks interleukin 1 activity," *J. Immunol.* 139:(10)3473–3483 (1987).

Schmid et al., "Induction of mRNA for a serine protease and a β–thromboglobulin–like protein in mitogen–stimulated human leukocytes[1]" *J. Immunol.* 139:250–256 (19870.

Walz et al., "Purification and amino acid sequencing of NAF, a novel neutrophil–activating factor produced by monocytes," *Biochem. Biophys. Res. Comm.* 149:(2):755–761 (1987).

Yoshimura et al., "Neutrophil chemotactic factor produced by lipopolysaccharide (LSP)–stimulated human blood mononuclear leukocytes: partial characterization and separation from interleukin 1 (IL 1)" *J. Immunol.* 139(3):788–793 (1987).

Yoshimura et al., "Purification of a human monocyte–derived neutrophil chemotactic factor that has peptide sequence similarity to other host defense cytokines," *Proc. Natl. Acad. Sci. USA* 84:9233–9237 (1987).

Kanamari et al., "Expression and excretion of human pancreatic secretory trypsin inhibitor in lipoprotein–delection mutant of *Escherichia coli,*" *Gene* (1988) 66:295–300 (1988).

Matsushima et al., "Molecular cloning of a human monocyte–derived neutrophil chemotactic factor (MDNCF) and the induction of MDNCF mRNA by interleukin 1 and tumor necrosis factor," *J. Exp. Me.* 167:1883–1893 (1988).

Schall et al., "A human T cell–specific molecule is a member of an new gene family," *J. Immunol.* 141(3):1018–1025 (1988).

Schroder et al., "Identification of different charged species of a human monocyte derived neutrophil activating peptide (MONAP)," *Biochem. Biophys. Res. Comm.* 152(1)277–284 (1988).

Thelen et al., "Mechanism of neutrophil activation by NAF, a novel monocyte–derived peptide agonist," *FASEB J.* 2:2702–2706 (1988).

Yoshimura, et al., "Human monocyte chemoattractant protein–1 (MCP–1)," *FEBS Lett.* 244(2):487–493 (1989).

Brown et al., "A family of small inducible proteins secreted by leukocytes are members of an new superfamily that includes leukocyte and fibroblast–derived inflammatory agents, growth factors, and indicators of various activation processes," *J. Immunol.* 142:679–687 (1989).

Maunder et al., "Pulmonary infection and inflammation during the adult respiratory distress syndrome (ARDS)," *Am. Rev. Respir. Dis.* 139:A221 (1989).

Nakoa et al., "Structures of human genes coding for cytokine LD78 and their expression," *Mol. Cell. Biology* 10(7):3646–3658 (1990).

Van Damme et al., A novel, $NH_2$–terminal sequence–characterized human monokine nuetrophil chemotactic, skin–reactive, and granulocytosis–promoting activity, *J. Exp. Med.* 167:1364–1376 (1988).

Lee et al., "Functional analysis of the endothelin–1 gene promoter," *J. Biol. Chem.* 265(18):10446–10450 (1990).

Mullins, "Fulminant hypertension in transgenic rats harbouring the mouse Ren–2 gene," *Nature* 344:541–544 (1990).

Fan et al., "Mapping small DNA sequences by fluorescence in situ hybridization directly on banded metaphase chromosomes," *Proc. Natl. Acad. Sci. USA* 87:6223–6227 (1990).

Antoniades et al., "Expression of monocyte chemoattractant protein 1 mRNA in human idiopathic pulmonary fibrosis," *Proc. Natl. Acad. Sci. USA* 89:5371–5375 (1992).

Koch et al., Enhanced production of monocyte chemoattractant protein–1 in rheumatoid arthritis, *J. Clin. Invest.* 90:772–779 (1992).

Lee et al., "Myosin light chain–2 luciferase transgenic mice reveal distinct regulatory programs for cardiac and skeletal muscle specific expression of a single contractile protein gene," *J. Biol. Chem.* 267(22):15875–15885 (1992).

Van Damme et al., "Structural and functional identification of two human, tumor derived monocyte chemotactic proteins (MCP–2 and MCP–3) belonging to the chemokine family," *J. Exp. Med.* 176:59–65 (1992).

Michiel, Dennis, "Chemokines: the missing link," *BIO/TECHNOLOGY* 11(6):739 Jun. 1993.

Gillitzer et al., "MCP–1 mRNA expression in basal keratinocytes of psoriatic lesions," *J. Invest. Dermatol.* 101(2):127–31 (1993).

Minty et al., "Molecular cloning of the MCP–3 chemokine gene and regulation of its expression," *Eur. Cytokine Netw.* 4:99–110 (1993).

Sousa et al., "Increased expression of the monocyte chemoattractant protein–1 in bronchial tissue from asthmatic subjects," *Am. J. Resp. Cell. Mol. Biol.* 10:142–147 (1994).

Rovin et al., "Glomerular expression of monocyte chemoattractant protein–1 in experimental and human glomerulonephritis" *Lab. Invest.* 71(4):536–42 (1994).

Westphal, H. "Transgenic mammals and biotechnology," FASEB J., vol. 3:117–120, 1989.

Korfhagen et al. "Cis acting sequences from a human surfactant protein gene confer pulmonary specific gene expression in transgenic mice," *Proc. Natl. Acad. Sci.,* vol. 87:6122–6126, 1990.

Dent et al. "Eosinophilia in Transgenic Mice Expressing Interleukin 5," *J. Exp. Med.,* vol. 172: 1425–1431, Nov. 1990.

Metcalf et al. "The Excess Numbers of Peritoneal Macrophages in Granulocyte Macrophage Colony Stimulating Factor Transgenic Mice are Generated by Local Proliferation," *J. Exp. Med.*, vol. 175:877–884, Apr. 1992.

Nakamura et al. "Constitutive production of MCP–1 and gro–alpha chemokines in basal epidermis of transgenic mice," J. of Inves. Derm. vol. 102(4): 525, Apr. 1994.

Rutledge et al. "Transgenic mice overexpressing murine MCP–1," Blood, vol. 82 (10 Suppl. 1): 187A, Dec. 1993.

Kappel et al. "Regulating gene expression in transgenic animals," Current Opinion in Biotechnology, vol. 3: 548–553, 1992.

TRANSGENIC MICE EXPRESSING ALVEOLAR MCP-1

STATEMENT AS TO FEDERALLY SPONSORED RESEARCH

This invention was made, in part, with Government support under Grant No. K11 HL02388, awarded by the National Institutes of Health. The Government may have certain rights in this invention.

FIELD OF THE INVENTION

This invention relates generally to chemotactic and cellular activating mechanisms which lead to mononuclear cell inflammation and transgenic mice used in the study of such. More particularly it relates to transgenic mice which overexpress gene such as human Monocyte Chemoattractant Protein-1 (MCP-1) in type II pulmonary epithelial cells which are useful in the study of a wide range of diseases which involve ligand-human receptor interaction.

BACKGROUND OF THE INVENTION

Inflammation is the reaction of living tissue to infection or injury, normally resulting in healing and the restoration of tissue structure in healing and the restoration of tissue structure and function. Inflammation also involves a complex set of responses which neutralize and remove pathogens and lead to the repair of the affected area. Symptoms of inflammation include pain, heat, redness, swelling, and dysfunction. Vascular dilation occurs, together with exudation of fluid and certain cellular components of blood into the surrounding tissue.

Most inflammatory states are characterized by the presence of leukocytes. In the early stages of inflammation, neutrophils, or polymorphonuclear leukocytes predominate. These are important in phagocytizing both wound debris and bacterial contaminants.

As inflammation progresses and the wound healing process begins, mononuclear leukocytes such as monocytes and lymphocytes are recruited to the area of inflammation. Lymphocytes recognize specific antigens to which they respond by secreting antibodies or soluble factors, known as cytokines, which mediate the inflammatory process. Monocytes, upon entering an area of inflammation, differentiate into tissue macrophages. These cells perform a wide range of functions including further phagocytosis of debris, secretion of cytokines, secretion of growth and mitogenic factors, and stimulation of connective and granulation tissue production.

In response to some inflammatory stimuli, mononuclear leukocytes predominate throughout the course of inflammation. These conditions are referred to as chronic inflammatory states. Examples of this range from chronic infections, such as tuberculosis and some fungal infections, to chronic noninfectious injuries such as occurs in atherosclerosis and some autoimmune diseases.

Inflammation is associated with a number of disease states. In some diseases, such as pneumonia, inflammation is important for the eradication of infection and the ultimate survival of the patient. In other diseases, unchecked inflammation may be detrimental. This can be caused by oxidants and proteolytic enzymes released by PMN's and macrophages, the continued release of pro-inflammatory cytokines by lymphocytes and macrophages, or excessive production of cell growth and connective tissue production stimulated by macrophages. In these later cases, a reduction of inflammation is beneficial to the patient. Examples of such disease states include arthritis and other inflammatory joint diseases, atherosclerosis, and idiopathic pulmonary fibrosis.

Recently, a family of low molecular weight proteins has been discovered which serve to attract leukocytes to sites of tissue injury or inflammation. These chemotactic cytokines, or chemokines, are produced by cells in response to local injury and stimulate the migration of leukocytes from the bloodstream into the injured tissue. Based on protein sequence homology, chromosomal location, and functional studies, chemokines fall into two classes.

Alpha, or CXC, chemokines are characterized by a conserved pair of cysteine residues in the N terminal region separated by a single amino acid (thus CXC). In general, CXC chemokines stimulate neutrophil chemotaxis and have been found to be produced in conditions associated with acute inflammation. The most well studied member of the CXC chemokine family is IL-8 (formerly NAP-1).

Beta, or CC chemokines have a conserved cysteine pair without an intervening amino acid (thus CC) and have been found to stimulate chemotaxis of monocytes and lymphocytes in vitro. The most well studied CC chemokine is Monocyte Chemoattractant Protein-1 (MCP1). Numerous studies have found increased levels of MCP-1 present in chronic inflammatory states. Examples include: psoriasis (Gillitzer et al., J. Invest. Dermatol. 101, 127–31, 1993), Rheumatoid Arthritis (Koch et al., J. Clin. Invest. 90, 772–9, 1992), Idiopathic Pulmonary Fibrosis (Antoniades et al., Proc. Natl. Acad. Sci. USA, 89, 5371–5, 1992), Atherosclerosis (Nelken et al., 1991), Asthma (Sousa et al., Am. J. Respir. Cell. Mol. Biol. 10, 142–7, 1994), glomerulonephritis (Rovin et al., Lab. Invest. 71, 536–42, 1994).

As stated above, MCP-1 acts in vitro to attract monocytes and lymphocytes and the accumulation of such cells is an integral part of the inflammatory process. The association of MCP-1 production with such a large number of inflammatory conditions suggests that MCP-1 plays a causal role. However, the exact in vivo effects of MCP-1 have not been demonstrated. Attempts to stimulate leukocyte accumulation by injection of MCP-1 into animals have not been consistently effective.

Lung inflammation is characterized by the presence of leukocyte in the pulmonary interstitium and airspaces. For example, interstitial and airspace neutrophils are a hallmark of adult respiratory distress syndrome (ARDS) (Pistorese, et al., Chest 88:A86, 1985; Maunder et al., Am. Rev. Resoir. Dis. 135:A260, 1987). Severity of ARDS is proportional to the number of neutrophils in the lungs, and patients who have fewer airspace neutrophils relative to airspace macrophages have a better rate of survival (Maunder et al., Am. Rev. Respir. Dis. 139:A221, 1989). Neutrophil and monocyte influx also appear to be involved in the pathogenesis of idiopathic pulmonary fibrosis (IPF) (Bitterman et al., J. Clin. Invest. 72:1801–1813, 1983; Hunninghakee et al., J. Clin. Invest. 68:259–269, 1981.

A major role for leukocytes in the symptoms of inflammation is suggested by studies of Job's syndrome, a congenital defect in PMN chemotaxis (Hill et al., Lancet 2:617–619, 1974). Patients with this condition experience recurrent "cold abscesses" without the usual associated symptoms of inflammation. In addition, patients with diabetes mellitus and patients receiving corticosteroid therapy have impaired leukocyte chemotaxis.

Two classes of chemotactically active molecules that can recruit PMN from the bloodstream into the lungs have been identified. A low molecular weight human lipid was identified by Hunninghake et al., (*J. Clin. Invest.* 66:473–483, 1980), and has subsequently been identified as leukotriene $B_4$ ($LTB_4$) (Martin et al., *Am. Rev. Respir. Dis.* 129:106–111, 1984;Martin et al., *J. Clin. Invest.* 80:1114–1124, 1987). A protein with a molecular weight of approximately 10,000 Daltons produced by human alveolar macrophages has been described (Merrill et al., *J. Clin. Invest.* 65:268–276, 1980).

Homologous low molecular weight (6–10 kDa) peptide chemoattractants have been isolated from LPS-stimulated human peripheral blood monocytes (Yoshimura et al., *J. Immunol.* 139:788–793, 1987; Schroder et al., *J. Immunol.* 139:3473–3483, 1987; Yoshimura et al., *Proc. Natl. Acad. Sci. Med. USA* 84:9233–9237, 1987; Matsushima et al., *J. Exp. Med.* 167:1883–1893, 1988; Walz et al, *Biochem. Biophys. Res. Comm.* 149:755–761, 1987; Thelen et al., *FASEB J.* 2:2702–2706, 1988; Peveri et al., *J. Exp. Med.* 167:1547–1549, 1988; Lindley et al., *Proc. Natl. Acad. Sci. USA* 85:9199–9203, 1988; Van Damme et al., *J. Exp. Med.* 167:1364–1376, 1988; Schroder et al., *Biochem. Biophys. Res. Comm.* 152:277–284, 1988) that are identical to the amino acid sequence inferred from the 3–10C cDNA sequence reported by Schmid et al., (*J. Immunol.* 139:250–256, 1987). The protein has now been called NAP-1.

In order to study the inflammatory process and create an environment in which anti-inflammatory drugs could be tested, the present invention was undertaken.

SUMMARY OF THE INVENTION

A transgenic, non-human animal is provided which overexpresses a gene responsible for the accumulation of monocytes and lymphocytes. The animal is preferably a mammal and more preferably a mouse or rat. The transgene inserted into the animal may be any gene which when expressed results in an enhanced accumulation of monocytes and lymphocytes at the site of expression. The transgene preferably expresses human Monocyte Chemoattractant Protein (MCP-1) and more preferably overexpress hMCP-1 in type II pulmonary epithelial cells. The invention includes a DNA construct and a plasmid containing the construct with a particularly preferred version of the plasmid being referred to as SPC-MCP-1. The plasmid SPC-MCP-1 is comprised of a human promoter operatively linked to a human MCP-1 coding sequence. The transgenic animal provides a useful animal model for testing drugs for their efficacy and safety in the treatment of diseases and conditions which result in an unexpectedly high accumulation of monocytes and/or lymphocytes.

A object of the invention is to provide a transgenic non-human mammal which expresses an artificially inserted gene resulting in abnormally high accumulation of monocytes and lymphocytes at the site of expression.

Another object is to provide a gene construct and a vector containing the construct which can be inserted into the genome of a non-human mammal to create the transgenic animal model of the invention.

A specific object is to provide the vector SCP-MCP-1 which is useful in creating transgenic mice which are useful in assaying drugs.

A feature of the invention is that monocytes and lymphocytes will accumulate at the site of expression of the transgene.

An advantage of the invention is that potential MCP-1 inhibitors and/or blocking agents can be readily tested in an in vivo model that closely mimics a human by the use of a human gene for MCP-1.

Another object of the invention is to provide a method of assaying drugs for the efficacy in the treatment of diseases and/or conditions which result in an abnormally high level of monocyte and/or lymphocyte accumulation.

These and other objects, advantages and features of the present invention will become apparent to those persons skilled in the art upon reading the details of the DNA constructs, vectors, transgenic non-human animal and assays for using such as more fully set forth below with reference being made to the accompanying figures forming a part hereof.

DETAILED DESCRIPTION OF THE INVENTION

Before the present DNA constructs, vectors, transgenic animals and assays carried out using same are described, it is to be understood that the invention is not limited to the particular constructs, vectors, animals or assays described as such may, of course, vary. It is also to be understood that the terminology used herein is for the purpose of describing particular embodiments only, and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to the insertion of "a plasmid" includes the insertion of a large number of such plasmids, reference to "an antibody" includes reference to mixtures of antibodies and reference to "the method" includes one or more methods of the type generally described herein and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

Definitions

The term "transgene" is used herein to describe genetic material which has been or is about to be artificially inserted into the genome of a living animal, preferably a living mammal. The transgene is inserted in such a manner such that at least a portion of the inserted transgene can be operatively expressed in the animal and the expression can be detected. A preferred transgene includes genetic material (which is preferably linked to a promoter) which when expressed results in an abnormally high (two fold greater or more and preferably ten fold greater or more) accumulation of monocytes and/or lymphocytes at the site of expression in a manner such that the monocytes and/or lymphocytes can be readily collected i.e., they do not migrate into the surrounding tissue and can be removed from the surface where they accumulate. A particularly preferred transgene is comprised in part of a gene which expresses human Monocyte Chemoattractant Protein-1 (MCP-1).

The terms "host animal" and more particularly "host mammal" are used to describe animals which are used in the process of the present invention by having their genome genetically and artificially manipulated so as to include a transgene of the invention. For example, host animals include those belonging to a genus selected from Mus (e.g., mice), Rattus (e.g., rats), Oryctolagus (e.g., rabbits), and Mesocricetus (e.g., hamsters) which have their genome artificially and genetically altered by the insertion of a human Monocyte Chemoattractant Protein-1 (hMCP-1) gene or a corresponding gene. The host animal becomes a transgenic animal of the invention when an exogenous gene is operatively inserted into its genome which gene when expressed, results in an accumulation of monocytes and/or lymphocytes or other cells related to the inflammatory process.

Finally, though the particularly preferred invention used mice as the species for expression of the transgene, use of other species could be advantageous in certain situations. For example, several animal models of endothelial damage require the ability to perform intravascular procedures on the animals in question. Studying the effects of chemokines in this situation may require the use of larger transgenic animals such as rats (Mullins, J. J., Nature 344:541–544 (1990) or rabbits (Hammer, R. E., Nature 315: 68–683 (1985).

"Corresponding" means homologous to or substantially equivalent to the designated sequence.

"Genetic material" is a material containing any DNA sequence or sequences either purified or in a native state such as a fragment of a chromosome or a whole chromosome, either naturally occurring or synthetically or partially synthetically prepared DNA sequences, DNA sequences which constitute a gene or genes and gene chimeras, e.g., created by ligation of different DNA sequences.

"Exogenous genetic material" is a genetic material not obtained from or does not naturally form a part of the specific germ cells or gametes which form the particular zygote which is being genetically transformed.

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Gene" is the smallest, independently functional unit of genetic material which codes for a protein product or controls or affects transcription and comprises at least one DNA sequence.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

"Zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism. The origin of the zygote can be from either the plant or animal kingdom.

"Parthenogenesis" is any technique that allows for the development of a female or male gamete into a cell and its development into an organism, which technique is different from the natural development of female and male gametes.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about replication and/or expression of the attached segment. An "expression vector" refers to a vector capable of autonomous replication or integration and contains control sequences which direct the transcription and translation of the "transgene" (e.g., MCP-1) in an appropriate host.

A "coding sequence" is a polynucleotide sequence which is transcribed and/or translated into a polypeptide.

A "promoter sequence" is a DNA regulatory region capable of binding RNA polymerase and initiating transcript of a downstream (i.e. in the 3' direction) coding sequence.

A coding sequence is "under the control" of the promoter sequence in a cell when transcription of the coding sequence results from the binding of RNA polymerase to the promoter sequence; translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence.

"Control sequences" refers to those sequences which control the transcription and/or translation of the coding sequence(s); these may include, but are not limited to, promoter sequences, transcriptional initiation and termination sequences, and translational initiation and termination sequences. In addition, "control sequences" refers to sequences which control the processing of the polypeptide encoded within the coding sequence; these may include, but are not limited to sequences controlling secretion, protease cleavage, and glycosylation of the polypeptide.

"Transformation" is the insertion of an exogenous polynucleotide (i.e., the transgene) into a host cell. The exogenous polynucleotide may be maintained as a plasmid, or alternatively, may be integrated within the host genome.

Overview

Transgenic animals of the present invention have actually been produced. More specifically, transgenic mice have been produced using the plasmid SPC-MCP-1 shown in FIG. 1. The plasmid contains the transgene which expresses human Monocyte Chemoattractant Protein-1 (hMCP1) operatively connected to a 3.7 kilobase promoter fragment (i.e., human Surfactant Protein C promoter) and the human growth hormone poly-adenylation site. Multiple copies of the plasmid SPC-MCP-1 were produced using conventional cloning procedures. The plasmids were digested with restriction enzymes and fragments containing (1) DNA encoding hMCP-1 (2) the promoter and (3) the human growth hormone poly-adenylation site were purified. The purified fragments were injected into the male pronucleus of fertilized mouse eggs. The injected mouse eggs are implanted into foster mothers. The progeny of the foster mothers were screened for the incorporation of the injected transgene fragments using slot blot analysis of tail DNA with a rabbit betaglobin intron probe. Positives were confirmed by Southern blot analysis. Mice which were confirmed as having the transgene incorporated in their genome were used as founders to create lines of transgenic mice which expressed MCP-1. These transgenic mice were screened for the expression of MCP-1 using Northern Blot analysis of total lung RNA using a human MCP-1 probe. Thereafter, MCP-1 protein expression was confirmed by Western Blot analysis of bronchoalveolar lavage fluid using antibodies against human MCP-1.

The above description relates to producing a specific transgenic animal using a specific animal host, transgene, plasmid and procedure. However, the present invention is broader in scope i.e., and can be applied to a wide range of animal hosts, using a wide range of plasmids and transgenes applied by different methodologies. The following is provided so as to disclose and describe a representative number of examples of alternate materials and procedures which are useful in connection with the present invention.

Vectors and Promoters

Figure 1:
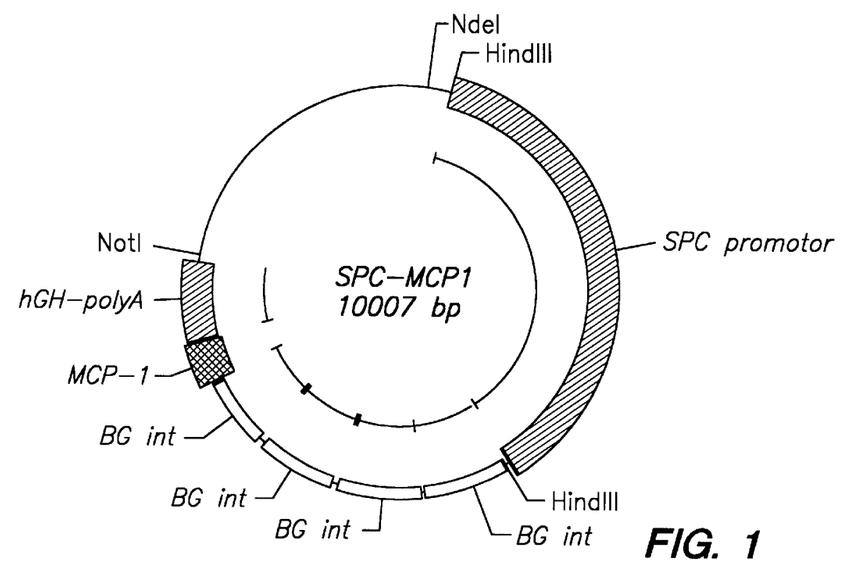
FIG. 1 is a schematic representation of a plasmid of the present invention which can be used in the production of a transgenic animal of the invention.

A particularly preferred plasmid of the invention is shown in FIG. 1 as SPC-MCP-1 which uses pUC18 as its vector backbone. Other plasmids can be created using as their backbones a variety of known vectors generally used for such. Examples of vectors which can be modified to include MCP-1 and used for cloning and host cells which they can transform include the bacteriophage $\lambda$ (*E. Coli*), pACYC 177 (*E. coli*), pKT 230 (gram-negative bacteria), pGV1106 (gram-negative bacteria), pLAFRI (gram-negative bacteria, pME 290 (non-*E. coli* gram-negative bacteria), pHV 14 (*E. coli* and *Bacillus subtilis*), pBD9 (Bacillus), pIJ61 (Streptomyces), pUC6 (Streptomyces) actinophage $\phi$C31 (Streptomyces), YIp5 (Saccharomyces), YCp19 (Saccharomyces), and bovine papilloma virus (mammalian cells).

In creating an expression vector the sequence encoding the transgene (e.g., the gene encoding hMCP-1) is located in the vector with the appropriate control sequences. The positioning and orientation of the coding sequence with respect to the control sequences is such that the coding sequence is transcribed under the control of the control sequences: i.e., the promoter will control the transcription of the mRNA derived from the coding sequence; and the ribosomes will bind at the ribosomal binding site to begin the translational process; and the stop coding codon used to terminate translation will be upstream from the transcriptional termination codon.

In designing plasmids for use in transgenic animals, control sequences and promoters are often used which direct transgene transcription to specific organs and cell types. The particularly preferred plasmid of the invention uses the Surfactant Protein C promoter to direct expression to type II alveolar cells and bronchiolar epithelial cells of the lung. Several promoters are known in the art which could be used for the tissue specific expression of mononuclear leukocyte chemoattractants. Examples include but are not limited to: the albumin promoter for liver (Pinkert et al., Genes Dev. 1:268–276, 1987), the endothelin promoter for endothelial cells (Lee ME et al., J. Biol. Chem, 265(18):10446–50 (1990), the keratin promoter for epidermis, the myosin light chain-2 promoter for heart (Lee K. J. et al., J. Biol. Chem, 267(22):15875–85 (1992), and the insulin promoter for pancreas (Bucchini, et al., PNAS USA 83:2511–2515, 1986).

Commonly used prokaryotic control sequences include such commonly used promoters as the $\beta$-lactamase (penicillinase) and lactose (lac) promoter systems (Chang et al, *Nature* (1977) (198:1056) and the tryptophan (trp) promoter system (Goeddel et al., *Nucleic Acids Res* (1980) 8:4057) and the lambda-derived $P_L$ promoter and N-gene ribosome binding site Shimatake et al., *Nature* (1981) 292:128). Control sequences for yeast vectors include promoters for the synthesis of glycolytic enzymes (Hess et al., *Adv Enzyme Reg.* (1986) 7:149; Holland et al., *Biochemistry* (1978) 17:4900). Additional promoters known in the art include the promoter for 3-phosphoglycerate kinase (Hitzeman et al., *J. Biol. Chem.* (1980) 255:2073). Other promoters, which have the additional advantage of transcription controlled by growth conditions and/or genetic background are the promoter regions for alcohol dehydrogenase 2 (ADH2), isocytochrome C, acid phosphate, degradative enzymes associated with nitrogen metabolism, the alpha factor system and enzymes responsible for maltose and galactose utilization. It is also believed terminator sequences are desirable at the 3' end of the coding sequences. Such terminator are found in the 3' untranslated region following the coding sequences in yeast-derived genes. Expression vectors for mammalian cells such as VERO, Hela or CHO cells, ordinarily include promoters and control sequences compatible with such cells as, for example, the commonly used early and late promoters from Simian Virus 40 (SV40) (Fiers et al, *Nature* (1978) 273:113), or other viral promoter such ass those derived from polyoma, adenovirus 2, bovine papilloma virus, or avian sarcoma viruses. The controller promoter, hMTII (Karin, M., et al., *Nature* (1982) 299:797–802) may also be used.

Transgenes

The preferred transgene is MCP-1 and more particularly hMCP-1. However, the transgene may be any exogenous genetic material which when operatively inserted into the host animal's genome will, when expressed, results in the accumulation of cells such as monocytes, lymphocytes or polymorphonuclear leukocytes (PMN) at the site of expression.

Other transgenes could be used which would both demonstrate the in vivo activity of the substance in question and lead to the accumulation of mononuclear leukocytes and/or other cell types. Examples include: RANTES (Schall, et al., J. Immunol. 141:1018–1025, 1988), macrophage inflammatory protein-1 alpha (MIP1) Nakoa, et al., Mol. Cell. Biol. 10:3646–3658, 1986), MIP1 beta (Brown, et al., J. Immunol. 142:679, 1989), MCP-2 (Van Damme, et al., J. Exp. Med. 176:59–65, 1992), and MCP-3 (Minty, et al., Eur. Cytokine Netw. 4:99–110, 1993, MARC, and FIC. Other useful transgenes include those referred to above in the "Background" and alveolar macrophage-derived chemotactic factor I (AMCF-1) as per U.S. Pat. No. 5,241,049.

There are two basic groups of proteins which have been identified as being associated with the accumulation of blood cells as a part of the inflammatory process. These are referred to generally as the (1) Chemokine a family and (2) Chemokine $\beta$ family. In connection with the present invention it is preferable to use transgenes which encode a chemokine $\beta$ family protein. Examples of chemokine $\alpha$ proteins are put forth below:

PF4, NAP-4, hNAP-2, hGRO $\alpha$/MGSA, hGRO $\beta$/hMIP2$\alpha$, hGRO/hMIP2$\beta$, hIL-8/NAP-1.

Examples of chemokine $\beta$ proteins are put forth below:

mTCA3, MP500(TCA3v), hRANTES, mRANTES, hI-309, mClO, LO78/(hMIP$\alpha$), mMIP$\alpha$, MAD-5$\beta$, MAD-5$\alpha$, hACT2(pAT744), hMP1$\beta$(hH400), mMIP1$\beta$, hMCP3, hHC14(nMCP2), bo MCP-1, ab MCP-1, a MCP-1, mE, H-CAR-MCP-1, Ost50surcMCP-1, mMARC, hRC.

A list of chemokine α and chemokine β proteins and variants thereof (along with references describing such in detail) is contained in BIO/TECHNOLOGY, Vol. 11, page 739, June 1993 which is incorporated herein by reference to disclose and describe useful transgenes.

Transgenic Animal Produced

The transgenic organisms of the invention all include within a plurality of their cells a cloned recombinant or synthetic DNA sequence which expresses a sequence which results in the accumulation of monocytes and/or lymphocytes. More specifically, the transgenic organisms contain specific sequences of exogenous genetic material, such as the sequences described above in detail which are comprised of a tissue specific promoter sequence and a sequence which encodes for production of a protein which results in monocyte and/or lymphocyte accumulation. Since it is possible to produce transgenic organisms of the invention utilizing one-or more of the above-described sequences, a general description will be given of the production of transgenic organisms by referring generally to exogenous genetic material. This general description can be adapted by those skilled in the art in order to incorporate the above-described specific DNA sequences (e.g., MCP-1) into organisms (e.g., mice) and obtain expression of those sequences utilizing the methods and materials described below. For more details regarding the production of transgenic organisms, and specifically transgenic mice, refer to U.S. Pat. Nos. 4,873,191, issued Oct. 10, 1989, U.S. Pat. No. 5,387,742, issued Feb. 28, 1995 (incorporated herein by reference to disclose methods producing transgenic mice), and to the numerous scientific publications referred to and cited therein.

The exogenous genetic material may be placed in either the male or female pronucleus of the zygote. More preferably, it is placed in the male pronucleus as soon as possible after the sperm enters the egg. In other words, insertion should be carried out right after the formation of the male pronucleus when the pronuclei are clearly defined and are well separated, each being located near the zygote membrane. The male pronucleus of a fertilized mouse egg is the preferred site for addition of the exogenous genetic material of the present invention.

It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material could then be added to the ovum or the decondensed sperm could be added to the ovum with the exogenous genetic material being added as soon as possible thereafter.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the DNA sequences which are added to the zygote is dependent upon the total amount of exogenous genetic material added and will be the amount which enables the genetic transformation to occur. Theoretically only one copy is required; however, generally, numerous copies are utilized for examples 1,000–20,000 copies of a gene in order to insure that one copy is functional. As regards the present invention, there is generally an advantage to having more than one functioning copy of each of the inserted exogenous DNA sequences to enhance the phenotypic expression of the exogenous DNA sequences (i.e., to obtain ubiquitous expression of the transgene which expresses a protein which results in the accumulation of monocytes and/or lymphocytes or other cells which accumulate as part of the inflammatory response.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

The transgenic mammals produced in accordance with the present invention will include exogenous genetic material. The exogenous genetic material will be a DNA sequence which results in the production of MCP-1 or a related protein. Further, the sequence will be attached to a promoter which promoter preferably allows the expression of the MCP-1 or a related protein in a specific type of cell such as a lung cell and may include a promoter which allows expression within a particular type of alveolar cell of the lung, e.g., type II alveolar cells of the lung.

In some preferred embodiments of the invention the transgenic animal includes a cell specific promoter in connection with a DNA sequence which results in the production of a MCP-1 or a related protein. A number of examples of such precursor proteins are disclosed and described. As a particularly preferred example of a transgenic mammal of the invention there is provided transgenic mammals which include DNA sequences capable of producing all or any of the proteins as described above.

The sequences are preferably included in connection with a promoter as also described above. However, other promoters which allow for cell-specific expression and particularly lung cell-specific and still more particularly certain types of lung cell-specific expression are preferred embodiments of the invention.

In yet another preferred embodiment of the invention the transgenic mammal includes a sequence which is capable of producing the MCP-1 or a related protein. This unique sequence may be produced in connection with all types of promoters. Transgenic mammals containing sequences capable of expressing MCP-1 or related proteins were not known prior to the present invention. Particularly preferred embodiments of the invention include sequences capable of producing A4i proteins which sequences are connected to cell-type specific promoters such as lung cell-specific promoters and still more particularly in connection with particular types of lung cell-specific promoters.

Methods and Materials

Most of the techniques which are used to transform cells, construct vectors, extract messenger RNA. prepare cDNA, and the like are widely practiced in the art, and most practitioners are familiar with the standard resource materials as well as specific conditions and procedures. However. for convenience, the following paragraphs may serve as a guideline.

Hosts and Control Sequences

Both procaryotic and eucaryotic systems may be used to express the desired transgene such as MCP-1 and related sequences; procaryotic hosts are, of course, the most convenient for cloning procedures. Procaryotes most frequently are represented by various strains of *E. coli* however, other microbial strains may also be used. *E coli* strains may secrete MCP-1 to the periplasm when the genes encoding these proteins are fused to appropriate signal peptides, and certain *E. coli* strains, for example, a lipoprotein mutant strain such as JE5505 (Kanamari, T. Gene (1988) 66:295–300), will excrete certain chimeric proteins directly to the culture medium.

Plasmid vectors which contain replication sites selectable markers and control sequences derived from a species compatible with the host are used; for example, *E. coli* is typically transformed using derivatives of pBR322, a plasmid derived from an *E. coli* species by Bolivar, et al., *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the β-lactamase (penicillinase) and lactose (lac) promoter systems (Chang, et al, *Nature* (1977) 198:1056) and the tryptophan (trp) promoter system (Goeddel et al *Nucleic Acids Res* (1980) 8:4057) and the lambda derived $P_L$ promoter and N-gene ribosome binding site (Shimatake. et al., Nature (1981) 292:128).

Other procaryotic control sequences include signal sequences which direct secretion of a protein to the periplasm. Commonly used bacterial signal peptides include the ompA (Kikuchi. et al, *Nucleic Acids Res* (1981) 9:5671–5678) and phoA (Beck and Bremer, *Nucleic Acids Res* (1980) 8:3011–3024) signal peptides which can be fused to a transgene sequence of the invention.

In addition to bacteria, eucaryotic microbes, such as yeast, may also be used as hosts. Laboratory strains of *Saccharomyces cerevisiae* Balker's yeast, are most used although a number of other strains or species are commonly available. Vectors employing, for example the 2 m origin of replication of Broach, J. R, *Meth Enz* (1983) 101:307, or other yeast compatible origins of replication (see, for example, Stinchcomb, et al., *Nature* (1979) 282:39, Tschumper, C., et al., *Gene* (1980) 10:157 and Clarke, L., et al., *Meth Enz* (1983) 101:300) may be used. Control sequences for yeast vectors include promoters for the synthesis of glycolytic enzymes (Hess, et al., *J. Adv Enzyme Reg* (1968) 7:149; Holland, et al., *Biochemistry* (1978) 17:4900). Additional promoters known in the art include the promoter for 3-phosphoglycerate kinase (Hitzeman, et al., *J Biol Chem* (1980) 255:2073) . Other promoters, which have the additional advantage of transcription controlled by growth conditions and/or genetic background are the promoter regions for alcohol dehydrogenase 2, isocytochrome C, acid phosphatase degradative enzymes associated with nitrogen metabolism, the alpha factor system and enzymes responsible for maltose and galactose utilization. It is also believed terminator sequences are desirable at the 3' end of the coding sequences in yeast-derived genes. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al., U.S. Pat. No. 4,399,216. These systems have the additional advantage of the ability to splice out introns and thus can be used directly to express genomic fragments. Useful host cell lines include VERO and HeLa cells and CHO cells. Expression vectors for such cells ordinarily include promoters and control sequences compatible with mammalian cells such as, for example, the commonly used early and late promoters from SV 40 (Fiers, et al., *Nature* (1978) 273:113), or other viral promoters such as those derived from polyoma, adenovirus 2, bovine papilloma virus, or avian sarcoma viruses The controllable promoter, hMTII (Karin, M., et al., *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA region. Origins of replication may be obtained, if needed, from viral sources. However integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* (1972) 69–7110 or the $RbCl^2$ method described in Maniatis, et al., *Molecular Cloning: A Laboratory Manual* (1982) Cold Spring Harbor Press, p. 254 and Hanahan, D., *J Mol Biol* (1983) 166:557–580 may be used for procaryotes or other cells which contain substantial cell wall barriers. For mammalian cells without such cell walls the calcium phosphate precipitation method of Graham and van der Eb, *Virology* (1978) 52:546, optionally as modified by Wigler, M., et al, *Cell* (1979) 16:777–785 may be used.

Transformations into yeast may be carried out according to the method of Beggs, 1. D., *Nature* (1978) 27S:104–109 or of Hinnen. A., et al., *Proc Natl Acad Sci (USA)* (1978) 75:1929.

Transformed cells are then grown under conditions which permit expression of the transgene and assembly of the expression product into a biologically active peptide such ass MCP-1 or other functionally equivalent peptide which acts to accumulate abnormally high levels of monocytes and/or lymphocytes or related cell types at the site of expression. The synthesized recombinant protein expressed by the transgene is then isolated from the host cells and purified. If the expression system secretes the protein expressed by this transgene into the growth media, the protein expressed by the transgene is isolated directly from the media. If the recombinant protein expressed by the transgene is not secreted, it is isolated from cell lysates. The selection of the appropriate growth conditions and recovery methods are within the skill in the art. With regard to purification, see for instance, EPA publication No. 0177957 and *Nature* (1986) 319:511–514.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299;and Jay, E., *J Biol Chem* (1984) 259:63–1.

Synthetic oligonucleotides are prepared by either the phosphotriester method as described by Edge, et al., *Nature* (supra) and Duckworth, et al, *Nucleic Acids Res* (1981) 9:1691 or the phosphoramidite method as described by Beaucage, S. L,., and Caruthers, M. H., *Tet Lett* (1981) 22:1859;and Matteucci, M. D., and Caruthers, M. H., *J Aam Chem Soc* (1981) 103:3185 and can be prepared using commercially available automated oligonucleotide synthesizes. Kinasing of single strands prior to annealing or for labeling is achieved using an excess, e.g., approximately 10 units of polynucleotide kinase to 1 nmole substrate in the presence of 50 mM Tris, pH 7.6, 10 mMMgCl$_2$, 5 mM dithiothreitol 1–2 mMATP, 1.7 pmoles γ32P-ATP (2.9 mCi/ mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs Product Catalog. In general, about 1 mg of plasmid or DNA sequence is cleaved by one unit of enzyme in about 20 ml of buffer solution, in the examples herein, typically, an excess or restriction enzyme is used to insure complete digestion of the DNA substrate. Incubation times of about one hour to two hours at about 37° C. are workable, although variations can be tolerated. After each incubation, protein is removed by extraction with phenol/ chloroform, and may be followed by ether extraction, and the nucleic acid recovered from aqueous fractions by precipitation with ethanol. If desired size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mMNaC:1 6 mM MgCl$_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with Si nuclease or BAL-31 results in hydrolysis of any single-stranded portion.

Ligations are performed in 15–50 ml volumes under the following standard conditions and temperatures: for example, 20 mM Tris-HCl pH 7.5, 10 mMMgCl$_2$ 10 mM DTT, 33 μ/ml BSA, 10 mM-50 mMNaCl, and either 40 μM ATP, 0.01–0.02 (Weiss) units T4 DNA ligase at 0° C. (for "sticky end" ligation) or 1 mMATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations are performed at 1 mM total ends concentration.

In vector construction employing "vector fragments", the vector fragment is commonly treated with bacterial alkaline phosphate (BAP) or calf intestinal alkaline phosphatase (CIAP) in order to remove the 5' phosphate and prevent self-ligation of the vector. Digestions are conducted at pH 8 in approximately 10 mM Tris-HCl1, mM EDTA using about I unit of BAP or CIAP per mg of vector at 60° for about one hour. In order to recover the nucleic acid fragments, the preparation is extracted with phenol/chloroform and ethanol precipitated. Alternatively, relegation can be prevented in vectors which have been double digested by additional restriction enzyme digestion and separation of the unwanted fragments.

For portions of vectors derived from cDNA or genomic DNA which require sequence modifications site specific primer directed mutagenesis may be used (Zoller, M. J., and Smith M. *Nucleic Acids Res* (1982) 10:6487–500 and Adelman, J. P., et al., *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Regulatory Sequences

In addition to control sequences, it may be desirable to add regulatory sequences which allow for regulation of the expression of the transgene (e.g., MCP-1) relative to the growth of the host cell. Examples of regulatory systems are those which cause the expression of a gene to be turned on or off in response to a chemical or physical stimulus, including the presence of a regulatory compound. In prokaryotic systems these would include the lac and trp operator systems. In eukaryotic systems induction can occur in metallothionein genes with heavy metals and the Mouse Mammary Tumor Virus (MMTV) system with steroids. In these cases, the sequence encoding the transgene (e.g., a gene encoding MCP-1) would be placed in tandem with the regulatory element.

There are also selective elements which give rise to DNA amplification which in turn can result in higher levels of specific protein production. In eukaryotic systems these include the dihydrofolate reductase gene (dhfr) which is amplified in the presence of methotrexate, and adenosine deaminase (ADA) in the presence of deoxycorfomycin. In these cases the sequence encoding MCP-1 or biologically functional similar gene may either be present on the same plasmid or merely be cotransfected together with the selectable element to allow for integration within the host cell genome near each other.

Other types of regulatory elements may also be present in then vector, i.e., those which are not necessarily in tandem with the sequence encoding the transgene. An example is the SV40 enhancer sequence, which, by its mere presence, causes an enhancement of expression of genes distal to it.

Modification of the sequence encoding the transgene before its insertion into the replicon, may be desirable or necessary, depending upon the expression system chosen. For example, in some cases, it may be necessary to modify the sequence so that it may be attached to the control sequences with the appropriate orientation, i.e., to maintain the reading frame. In some cases, it may be desirable to add sequences which cause the secretion of the polypeptide from the host organism, with subsequent cleavage of the secretory signal. The techniques for modifying nucleotide sequences utilizing cloning are well known to those skilled in the art. They include, e.g., the use of restriction enzymes, of enzymes such as Ba131 to remove excess nucleotides, and of chemically synthesized oligonucleotides for use as adapters, to replace lost nucleotides, and in site directed mutagenesis.

The appropriately modified sequence encoding the transgene may be ligated to the control sequences prior to insertion into a vector. Alternatively, the coding sequence can be cloned directly into an expression vector which already contains the control sequences and an appropriate restriction site. For expression of the transgene in prokaryotes and in yeast, the control sequences will necessarily be heterologous to the coding sequence. In cases where the transgene is to be expressed in cell lines derived from vertebrates, the control sequences may either be heterologous or homologous depending upon the particular cell line.

Verification of Construction

In the constructions set forth below, correct ligations for plasmid construction may be confirmed by first transforming *E. coli* strain MC1061 obtained from Dr. M. Casadaban (Casadaban. M. et al., *J Mol Biol* (1980) 138:179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *Proc Natl Acad Sci* (*USA*) (1969) 62:1159, optionally following chloramphenicol amplification (ClewelL D. B., *J Bacteriol* (1972) 110:667). Several mini DNA preps are commonly used, e. g., Holmes, D. S., et al., *Anal Biochem* (1981) 114:193–197 and Birnboim, H C., et al., *Nucleic Acids Res* (1979) 7:1513–1523. The isolated DNA is analyzed by restriction and/or sequenced by the dideoxy nucleotide method of Sanger, F., et al., *Proc Natl Acad Sci* (*USA*) (1977) 74:5463 as further described by Messing, et al, *Nucleic Acids Res* (1981) 9:309, or by the method of Maxam, et al., *Methods of Enzymology* (1980) 65:499.

EXAMPLE

The following examples are put forth so as to provide those of ordinary skill in the art with a complete disclosure and description of how to make the constructs, vectors, transgenic animals and assays of the present invention and are not intended to limit the scope of what the inventors regard as their invention. Efforts have been made to ensure accuracy with respect to nomenclature and numbers used (e.g., amounts, temperature, etc.) but some experimental errors and deviation should be accounted for. Unless indicated otherwise, parts are parts by weight, molecular weight is weight average molecular weight, temperature is in degree centigrade, and pressure is at or near atmospheric.

Example 1

Producing The Vector SCP-MCP-1

FIG. 1 shows the vector SPC-MCP-1 contains the following DNA segments in the order listed: 1) A pUC18 vector backbone containing the segments needed for bacterial replication and drug selection. 2) The human Surfactant Protein C (SPC) promoter which directs expression of the transgene to type II alveolar cells (Proc. Nat. Acad. Sci.USA 87:6122–6126, 1990). 3) Four copies in a tandem repeat of the rabbit beta-globin intron (Proc. Nat. Acad. Sci.USA 78:1527–1531, 1981).

Intron directed splicing is meant to increase expression of the transgene. 4) The coding sequence for human Monocyte Chemoattractant Protein-1 (EBS Lett. 244: 487–493, 1989). 5) The human Growth Hormone polyadenylation site which provides the signal for proper RNA transcription termination and processing (DNA 1: 239–249, 1982).

These segments were assembled as follows to produce SPC-MCP-1. A 3.8 Kb HindIII-HindIII fragment of the SPC promoter was obtained in a pUCl8 vector in which the EcoRl site had been replaced with a NotI site (pUC18-SPC). The human Growth Hormone polyadenylation site was obtained as a 600 BP BglII-EcoRI fragment in an SP72 vector. This fragment was excised by digestion with BglII/XbaI and cloned into the Bam HI-XbaI site of pKS using a BglII-Bam HI linker to create pKS Poly A. pKS Poly A was digested with Bam HI and the 600 BP Bam HI-Bam HI fragment purified. This was cloned into the Bam HI site of pUC18-SPC in the correct orientation to obtain pUC18-SPC-Poly A.

A 650 bp Bam HI-EcoRI fragment of the rabbit beta-globin intron was obtained. New restriction sites were added to the ends by the use of XhoI-Bam HI and EcoRI-SalI adapters. This fragment was ligated into the SalI site of pUC18-SPC-Poly A between the SPC and Poly A segments. A clone was selected which had integrated four copies of the rabbit beta-globin intron in a head-to-tail tandem repeat (pUC18-SPC-BGI-Poly A). This eliminated all of the XhoI and SalI restriction sites except for a single SalI site at the downstream (3') end of the beta-globin intron.

The human MCP-1 coding sequence was obtained as a PCR generated XhoI-EcoRI fragment cloned into pSK+. This was excised as a 350 bp XhoI-BamHI fragment. pUC18-SPC-BGI-Poly A was digested with SalI and BglII (both sites between BGI and Poly A) and ligated to the MCP-1 fragment to obtain pUC18-SPC-BGI-MCP-Poly A which we designated as SPC-MCP-1.

Example 2

Production of Transgenic Mice

The vector SPC-MCP-1 was digested with NdeI and NotI. The 7.6 Kb fragment containing the SPC, BGI, MCP-1, and Poly A segments was purified on an agarose gel and electroeluted into TAE buffer. The fragment was then phenol and phenol/chloroform extracted, ethanol precipitated and resuspended in TE buffer at a concentration of 1.5 ug/ml. Fertilized eggs were obtained by superovulation and mating of C57B6/DBA2 F1 female mice. The above solution was microinjected into the pronuclei of one cell embryos. A total of 332 microinjected eggs were transferred at the two cell stage into the oviducts of pseudo-pregnant females at day one of gestation. Forty-three live born pups which survived to weaning were obtained.

Example 3

Verification of Transgene Insertion and Protein Production

All live born pups obtained from embryo injections were initially screened for incorporation of the SPC-MCP-1 transgene by slot blot hybridization. Briefly, genomic DNA was obtained by digestion of a 1 cm tail cut in lysis/digestion buffer at 55° C. overnight. Digests were centrifuged, undigested material pelleted, and supernatants were phenol/chloroform extracted and precipitated with isopropyl alcohol. Genomc DNA pellets were resuspended in 0.5 ml TE buffer. Aliquots were denatured with 0.8N NaOH and slot blotted onto Hybond-N+ membranes. A probe was obtained by random primer $P^{32}$-dCTP incorporation into a rabbit beta-globin intron fragment. The slot blot was prehybridized at 65 degrees centigrade for 1–2 hours and hyridized with probe in hybridization buffer (7% SDS, 0.25M $Na_2HPO_4$, 10% Dextran Sulfate, 100 ug/ml Salmon Sperm DNA) at 65 degrees centigrade overnight. Blots were then washed and placed on autoradiography film for 24 hours. Of forty-three live born pups were obtained by injection of the SPC-MCP construct, eight were found to be transgene positive by slot blot hybridization.

Mice positive for transgene incorporation by slot blot were confirmed by Southern Blotting. Genomic DNA obtained ss above was digested with EcoRI, run on a 1% agarose gel and transferred to Hybond-N+ membranes. Membranes were hybridized with the rabbit beta-globin intron fragment as described above. Mice confirmed positive for transgene incorporation were identified by the presence of a diagnostic 650 bp beta-globin intron fragment. All eight mice positive by slot blot hybridization were confirmed as such by Southern Blotting. These mice were used as founders to create eight continuous SPC-MCP-1 transgenic mouse lines.

To determine if the incorporated transgene was actively transcribed in the SPC-MCP-1 transgenic mouse lines, Northern Blot analysis was performed on the F1 progeny of founder matings. Lungs were excised from these mice and homogenized in guanidinium isothiocyanate solution. This was extracted with acid phenol/chloroform and precipitated with isopropyl alcohol to yield lung total RNA. Ten micrograms of lung total RNA from each mouse tested was run on a 0.8% RNA formaldehyde gel and transferred to a Hybond-N+ membrane. Membranes were hybridized with a $P^{32}$-dCTP probe obtained by random priming of the human MCP-1 coding region as described above. Six of eight founder mice were found to express MCP-1 at high levels as assessed by Northern blot hybridization of total lung RNA. To demonstrate that MCP-1 protein was actually expressed and secreted into the airways of transgenic mice, MCP-1 was immunopreciptated from bronchoalveolar lavage fluid obtained from transgenic mice using a mouse monoclonal antibody specific for human MCP-1. Immunoprecipitates were subjected to SDS-polyacrylamide gel electrophoresis, transferred to nitrocellulose, and western blotted using a rabbit polyclonal anti-MCP-1 antibody. High levels of human MCP-1 were found in the bronchoalveolar lavage fluid of SPC-MCP mice but not in that from nontransgenic littermates.

Example 4

Determination and Drug Manipulation of Transgenic Phenotype

Figure 2:
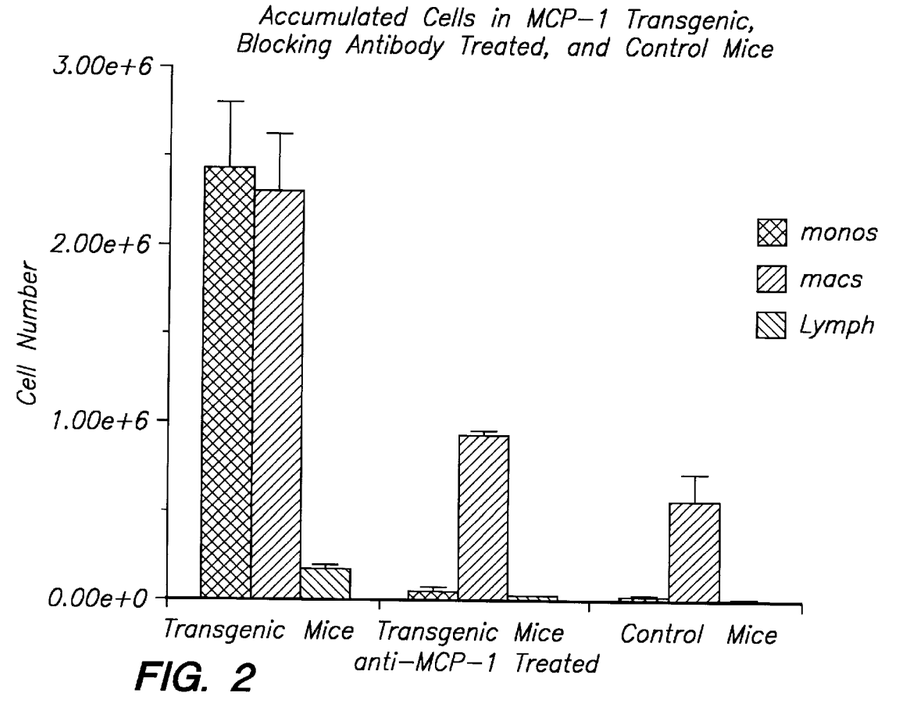
FIG. 2 is a graph showing a comparison of control mice, transgenic mice of the invention and a transgenic mice treated with anti-MCP-1 with respect to the accumulation of monocytes and lymphocytes.

To determine if SPC-MCP-1 transgenic mice displayed the predicted phenotype (accumulation of monocytes and lymphocytes in the lungs), counts were made of the cells present in the bronchoalveolar spaces of transgenic mice. Mice were anesthetized and their lungs and trachea surgically exposed. The trachea were cannulated with an 18 gauge angiocath and the lungs lavaged with a total of 5 ml of PBS in a series of 0.5–0.8 ml washes (bronchoalveolar lavage). Total cells obtained were counted in a hemocytometer. Aliquots of bronchoalveolar lavage fluid were cytospun onto microscope slides and air dried. Adherent cells were labeled with a series of cell type specific antibodies and stained using Alkaline Phosphatase conjugated secondary antibodies and peroxidase substrate color development kit (Vector DAB). The proportion of individual cell types were manually counted and multiplied by the total cell count to calculated the total number of cells of specific leukocytes type present in the mouse airspaces. SPC-MCP-1 mice demonstrated a near five hundred fold increase in the number of monocytes and a near one hundred fold increase in the number of lymphocytes over that seen in nontransgenic mice as shown in FIG. 2.

To determine if this phenotype could be modulated by external agents, we treated SPC-MCP-1 mice with a human MCP-1 blocking antibody. MCP-D92, a human MCP-1 blocking antibody developed in our lab, was produced by hybridoma culture, affinity purified using Protein A sepharose, and dialyzed against sterile PBS. SPC-MCP-1 mice were treated with daily intraperitoneal injections of 500 ug of MCP-D92 times seven days and subjected to bronchoalveolar lavage as described above. MCP-D92 injected mice demonstrated a near complete reversal of their phenotype as determined by bronchoalveolar cell counts as shown in FIG. 2.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A transgenic mouse whose somatic and germ cells comprise a transgene:

said transgene comprising a sequence encoding a mammalian monocyte chemoattractantprotein (MCP-1) operably linked to a surfactant protein C promoter, and at least one intron, wherein said transgene is expressed in the cells of the lung of said mouse and provides for an abnormally high level of accumulation of blood mononuclear leukocytes at the site of expression.

2. The transgenic mouse of claim 1, wherein the level of accumulation is ten times or more than the level of accumulation in the absence of the transgene.

3. The transgenic mouse of claim 1, wherein the transgene encodes human Monocyte Chemoattractant Protein-1 (hMCP-1).

4. The transgenic mouse of claim 1, wherein said lung cells are type II alveolar cells and bronchoalveolar epithelial cells.

5. A method of assaying a drug with respect to its ability to decrease the accumulation of blood cells associated with the inflammatory process, comprising:

administering the drug to a transgenic mouse whose somatic and germ cells comprises a transgene:

said transgene comprising sequence encoding a mammalian monocyte chemoattractantprotein (MCP-1) operably linked to a surfactant protein C promoter, and at least one intron, wherein said transgene is expressed in the cells of the lung of said mouse and provides for an abnormally high level of accumulation of blood mononuclear leukocytes at the site of expression; and determining the effect of the drug on the level of blood cell accumulation.

6. The method of claim 5, wherein the determining comprises collecting said accumulated cells and determining if the drug decreases the number of accumulated cells relative to a standard wherein the drug is not administered, wherein the transgene encodes human Monocyte Chemoattractant Protein-1 (hMCP-1).

* * * * *